US012705862B2

(12) United States Patent
Beaumont et al.

(10) Patent No.: US 12,705,862 B2
(45) Date of Patent: Aug. 11, 2026

(54) METHOD AND SYSTEM FOR AUTOMATIC CLASSIFICATION OF RADIOGRAPHIC IMAGES HAVING DIFFERENT ACQUISITION CHARACTERISTICS

(71) Applicant: MEDIAN TECHNOLOGIES, Valbonne (FR)

(72) Inventors: Hubert Beaumont, Valbonne (FR); Tiffany Foriel, Cannes (FR); Vincent Bobin, Pibrac (FR); Antoine Iannessi, Nice (FR)

(73) Assignee: MEDIAN TECHNOLOGIES, Valbonne (FR)

( * ) Notice: Subject to any disclaimer, the term of this patent is extended or adjusted under 35 U.S.C. 154(b) by 750 days.

(21) Appl. No.: 18/151,906

(22) Filed: Jan. 9, 2023

(65) Prior Publication Data

US 2023/0222771 A1 Jul. 13, 2023

(30) Foreign Application Priority Data

Jan. 10, 2022 (EP) .................................... 22315010

(51) Int. Cl.
*G06V 10/764* (2022.01)
*G06V 10/25* (2022.01)
(Continued)

(52) U.S. Cl.
CPC ............ *G06V 10/764* (2022.01); *G06V 10/25* (2022.01); *G06V 10/26* (2022.01); *G06V 10/44* (2022.01);
(Continued)

(58) Field of Classification Search
CPC ......... G06T 2207/20081; G06T 7/0012; G06T 2207/30096; G06T 2207/20084;
(Continued)

(56) References Cited

U.S. PATENT DOCUMENTS

2017/0193655 A1* 7/2017 Madabhushi ......... G06T 7/0012
2018/0068445 A1 3/2018 Fonte et al.
(Continued)

OTHER PUBLICATIONS

Beaumont et al., "Harmonization of radiomic feature distributions: impact on classification of hepatic tissue in CT imaging", European Radiology, vol. 31, No. 8, Jan. 18, 2021, pp. 6059-6068.
(Continued)

*Primary Examiner* — Alex Kok S Liew
(74) *Attorney, Agent, or Firm* — HAUPTMAN HAM, LLP

(57) ABSTRACT

A method and system are disclosed for generating a machine learning model for automatic classification of radiographic images acquired by various acquisition protocols. The method includes the steps of: providing a plurality of radiographic images, detecting and segmenting in each of the radiographic image at least one regions of interest (ROI) as reference ROI, measuring at least one radiomic feature per reference ROI, identifying valid reference ROIs based on the measured radiomics values, and clustering the measured radiomics values of valid reference ROIs into at least two reference clusters according to a set of characteristics of image acquisition. A method and system are disclosed for classifying radiographic images by applying a machine learning model generated for automatic classification of radiographic images.

24 Claims, 6 Drawing Sheets

(51) Int. Cl.

| | |
|---|---|
| ***G06V 10/26*** | (2022.01) |
| ***G06V 10/44*** | (2022.01) |
| ***G06V 10/762*** | (2022.01) |
| *A61B 5/055* | (2006.01) |

(52) U.S. Cl.
CPC ............ *G06V 10/762* (2022.01); *A61B 5/055* (2013.01); *G06V 2201/031* (2022.01)

(58) Field of Classification Search
CPC ......... G06T 2207/10081; G06T 7/0016; G06T 7/11; G06T 2207/10088; G06T 2207/10104; G06T 2207/30061; G06T 2207/30101; G06T 7/0014; G06T 2200/04; G06T 2207/20076; G06T 2207/30016; G06T 2207/30024; G06T 2207/30064; G06T 2207/30081; G06T 7/174; G06T 7/337; G06T 17/00; G06T 2207/10016; G06T 2207/10072; G06T 2207/10108; G06T 2207/10116; G06T 2207/10132; G06T 2207/20036; G06T 2207/30048; G06T 2207/30056; G06T 2207/30068; G06T 7/41; G06T 7/97; A61B 5/7267; A61B 5/055; A61B 6/032; A61B 5/4842; A61B 5/02007; A61B 5/4848; A61B 5/7275; A61B 2576/026; A61B 5/0033
See application file for complete search history.

(56) References Cited

U.S. PATENT DOCUMENTS

| | | | | |
|---|---|---|---|---|
| 2018/0096477 | A1 | 4/2018 | Avila | |
| 2019/0325621 | A1* | 10/2019 | Wang | A61B 6/037 |
| 2020/0003857 | A1* | 1/2020 | Weese | G01R 33/4828 |
| 2021/0018584 | A1 | 1/2021 | Golay et al. | |
| 2022/0404364 | A1* | 12/2022 | Madabhushi | G16H 50/70 |

OTHER PUBLICATIONS

Extended European Search Report issued in corresponding European Application No. 22315010.3, dated Jun. 23, 2022, pp. 1-10, European Patent Office, Munich, Germany.

* cited by examiner

METHOD AND SYSTEM FOR AUTOMATIC CLASSIFICATION OF RADIOGRAPHIC IMAGES HAVING DIFFERENT ACQUISITION CHARACTERISTICS

The present application claims priority to European Application No. 22315010.3, filed Jan. 10, 2022, the entirety of which is incorporated herein by reference.

TECHNICAL FIELD

The disclosure relates broadly to methods and frameworks for automatically classifying medical images acquired by various acquisition protocols.

The present disclosure more particularly relates to a machine learning model for the automatic classification of radiographic images according to a set of characteristics of image acquisition.

BACKGROUND

As part of the diagnostic evaluation, or patients monitoring by imaging, measurements are performed on the radiological images (CT, MRI, etc.) with a final objective of helping clinical decision-making. It has been observed that the diversity of hardware, software and acquisition parameters being used for image acquisition may lead to significant variability in radiological evaluations and thus creating uncertainty in subsequent clinical decisions.

As the reliability of the measurements being extracted from the images can contribute to the quality of the diagnosis, and then to the care of the patients, the control of the image acquisition at an earlier stage seems to be essential.

Several strategies have been proposed to reduce the variability of evaluations induced by the variety of acquisition protocols. However, a strong limitation of these strategies stands in the prior and precise knowledge of the acquisition protocols used, yet this knowledge is often difficult to obtain, and in some cases impossible.

It would be thus highly helpful to know how to control the impact of the image acquisition due to the variety of acquisition protocols without having prior knowledge of the acquisition protocols.

SUMMARY

According to a first aspect, disclosed is a method for generating a machine learning model for automatic classification of radiographic images acquired by various acquisition protocols, comprising the steps of:

- providing a plurality of radiographic images of at least two different patients, the radiographic images of each of the at least two different patients being acquired with acquisition protocols different from each other,
- detecting and segmenting, in each of the radiographic images at least one region of interest (ROI) as reference ROI, measuring at least one radiomics feature per reference ROI,
- identifying valid ROIs from a plurality of reference ROIs based on the measured radiomics values,
- clustering the measured radiomics values of the valid reference ROIs into at least two reference clusters according to a set of characteristics of image acquisition.

Thus said machine learning model for the automatic classification of radiographic images is achieved by defining at least two references clusters according to a set of characteristics of image acquisition.

In some examples, the plurality of radiographic images comprises at least one kind of the following: clinical images being acquired by imaging a patient, phantom images acquired by imaging a phantom object, and mixed images each combining a patient and a pocket phantom acquired by imaging a patient with a phantom object in proximity to the patient.

In some examples, the method further comprises, before the step of detecting and segmenting and after the step of providing a plurality of radiographic images, sorting the plurality of radiographic images into a first group and a second group, wherein the first group of radiographic images comprises clinical images and the second group of radiographic images comprises phantom images and/or mixed images each combining a patient and a pocket phantom.

In some examples, the first group of the plurality of radiographic images is used to generate a first machine learning model and the second group of the plurality of radiographic images is used to generate a second machine learning model.

In some examples, the method further comprises: before the step of detecting and segmenting at least one ROI as reference ROI, a step of pre-processing each of the radiographic images by using preferably at least one of the following image processing techniques: denoising, resampling, diffusion-weighted magnetic resonance imaging and apparent diffusion coefficient mapping.

In some examples, with the radiographic images being clinical images, detecting and segmenting in each of the radiographic images at least one ROI as reference ROI comprises detecting and segmenting in each clinical images at least one non-pathological ROI as reference ROI.

In some examples, the step of detecting and segmenting in each clinical image at least one non-pathological ROI as reference ROI, comprises segmenting various non-pathological anatomical structures of interest (ASIs), and segmenting and detecting ROIs in the segmented non-pathological ASIs.

In some examples, with the radiographic images being phantom images and/or mixed images each combining a patient and a pocket phantom, the step of detecting and segmenting in each of the radiographic images at least one regions of interest (ROI) as reference ROI comprises segmenting various phantom-derived structure of interest (PDSIs) based on a reference material, and segmenting and detecting (ROIs in the segmented PDSIs.

In some examples, the step of segmenting various phantom-derived structure of interest (PDSIs) further comprises generating a set of segmentation masks of PDSIs, and the step of segmenting and detecting ROIs in the segmented PDSIs comprises detecting and segmenting ROIs using the set of segmentation masks of PDSIs.

In some examples, the method further comprises, after the step of detecting and segmenting at least one non-pathological ROI as reference ROI, a step of optimizing at least one of the previously detected and segmented ROIs by implementing at least one image processing technique chosen among binning of image values and rescaling.

In some examples, the step of measuring at least one radiomic feature per reference ROI comprises radiomics computing of each reference ROI.

In some examples, the step of identifying valid ROIs from a plurality of reference ROIs further comprises comparing the measured radiomics values to a predetermined range of radiomics values preferably chosen from a set of reference value ranges and determining a valid ROI if the measured radiomics values thereof fall into the predetermined range of radiomics values.

In some examples, the set of reference value ranges comprises at least one reference value range each corresponding to the value range of a predetermined ASI for a predetermined acquisition modality.

In some examples, the step of clustering measured radiomics values of the valid reference ROIs into at least two reference clusters comprises a step of classifying the measurements of valid reference ROIs into at least two clusters.

In some examples, the step of clustering measured radiomics values of the valid reference ROIs into at least two reference clusters further comprises a step of characterizing the at least two clusters in order to obtain at least two reference clusters.

According to a second aspect, disclosed is a method for classifying at least one radiographic image according to a set of characteristics of image acquisition by applying a machine learning model generated for automatic classification of radiographic images, the machine learning model defining at least two reference clusters of the radiographic images acquired by various acquisition protocols, comprising the steps of: receiving at least one radiographic image, providing one of the at least one radiographic image as a candidate image for classification, detecting and segmenting in the candidate image at least one region of interest (ROIs) as candidate reference ROI, measuring at least one radiomic feature per candidate reference ROI, identifying valid candidate reference ROIs from a plurality of candidate reference ROIs based on the measured radiomics values, comparing the measured radiomics values of each the valid candidate reference ROIs to each of the radiomics value of each of the at least two reference clusters, and classifying the candidate image into one of the at least two reference clusters based on the comparison.

In some examples, the plurality of radiographic images comprises at least one kind of the following: clinical images being acquired by imaging a patient, phantom images acquired by imaging a phantom object, and mixed images each comprising a patient and a pocket phantom acquired by imaging a patient with a phantom object in proximity to the patient.

In some examples, the method comprises, before the step of detecting and segmenting and after the step of providing one of the at least one radiographic image as a candidate image for classification, selecting the machine learning model to be used based on the candidate image for classification.

In some examples, selecting the machine learning model to be used for classification comprising the steps of: determining that the machine learning model to be used is a first machine learning model being generated with clinical images if the candidate image is a clinical image; and determining that the machine learning model to be used is a second machine learning model being generated with phantom images and/or mixed images if the candidate image is an image of a phantom object or a mixed image of a patient with a pocket phantom.

In some examples, the machine learning model has been generated by implementing the method for generating a machine learning model according to the first aspect of the present disclosure.

In some examples, the method further comprises, before the step of detecting and segmenting at least one ROIs as candidate reference ROI, a step of pre-processing the candidate image by using preferably at least one of the following image processing techniques: denoising, resampling, diffusion-weighted magnetic resonance imaging and apparent diffusion coefficient mapping.

In some examples, the step of detecting and segmenting in the candidate image at least one regions of interest (ROI) as candidate reference ROI comprises, if it is determined that the machine learning model to be applied is the first machine learning model, detecting and segmenting in the candidate image at least one non-pathological regions of interest (ROI) as candidate reference ROI.

In some examples, the step of detecting and segmenting in the candidate image at least one non-pathological regions of interest (ROI) as candidate reference ROI comprises segmenting various non-pathological anatomical structure of interest (ASIs), and segmenting and detecting ROIs in the segmented ASIs as candidate reference ROIs.

In some examples, the step of segmenting various anatomical structure of interest (ASIs) further comprises generating a set of segmentation masks of ASIs, and the step of segmenting and detecting ROIs in the segmented non-pathological ASIs further comprises detecting and segmenting ROIs using the set of segmentation masks of ASIs.

In some examples, the step of detecting and segmenting in the candidate image at least one regions of interest (ROI) as candidate reference ROI comprises, if it is determined that the machine learning model to be applied is the second machine learning model, segmenting various phantom-derived structure of interest (PDSIs), and segmenting and detecting ROIs in the segmented PDSIs.

In some examples, the step of segmenting various phantom-derived structure of interest (PDSIs) further comprises generating a set of segmentation masks of PDSIs, and the step of segmenting and detecting ROIs in the segmented PDSIs comprises detecting and segmenting ROIs using the set of segmentation masks of PDSIs.

In some examples, the method further comprises, after the step of detecting and segmenting in the candidate image at least one regions of interest (ROI) as candidate reference ROI, a step of optimizing at least one of the previously detected and segmented candidate reference ROIs by at least one image processing technique chosen among binning of image values and rescaling.

In some examples, the step of identifying valid candidate reference ROIs from a plurality of candidate reference ROIs further comprises comparing the measured radiomics values to a predetermined range of radiomics values preferably chosen from a set of reference value ranges and determining a valid candidate reference ROI if the measured radiomics values thereof fall into the predetermined range of radiomics values.

In some examples, the step of comparing the measured radiomics values of each the valid candidate reference ROIs to each of the radiomics value of each of the at least two reference clusters comprises calculating a distances between the measured radiomics values of each of the valid candidate reference ROIs and each of the radiomics values of each of the at least two reference clusters.

In some examples, calculating of a distance between the measured radiomics values of each valid candidate reference ROIs to each of the radiomics values of each of the at least two reference clusters is implemented in accordance with a predetermined metric preferably chosen among: Manhattan metric, Euclidian metric and Minkowski metric.

In some examples, the step of classifying the candidate image into one of the at least two reference clusters based on the comparison comprises selecting the cluster having the smallest calculated distance and/or eliminating the cluster having the largest calculated distance.

A further aspect of the present disclosure relates to a non-transitory computer readable medium storing instructions which, when implemented by at least one digital processing device, performs at least the steps of the method according the first aspect of the invention and/or the method according the second aspect of the invention.

A further aspect of the present disclosure relates to a computer program product comprising instructions which, when implemented by at least one digital processing device, performs at least the steps of the method according the first aspect of the invention and/or the method according the second aspect of the invention.

A further aspect of the present disclosure relates to a computer-implemented system for automatic classification of radiographic images, comprising: at least one machine learning model being generated to classify at least one radiographic images according to a set of characteristics of image acquisition.

Other objects, features and advantages of the invention(s) disclosed herein, and their various embodiments/aspects, may become apparent in light of the descriptions of some exemplary embodiments that follows.

BRIEF DESCRIPTION OF THE DRAWINGS

Reference will be made in detail to embodiments of the disclosure, non-limiting examples of which may be illustrated in the accompanying drawing figures. Some figures may be in the form of diagrams. Some elements in the figures may be exaggerated; others may be omitted, for illustrative clarity.

Any text (legends, notes, reference numerals and the like) appearing on the drawings are incorporated by reference herein.

DETAILED DESCRIPTION

Figure 1:
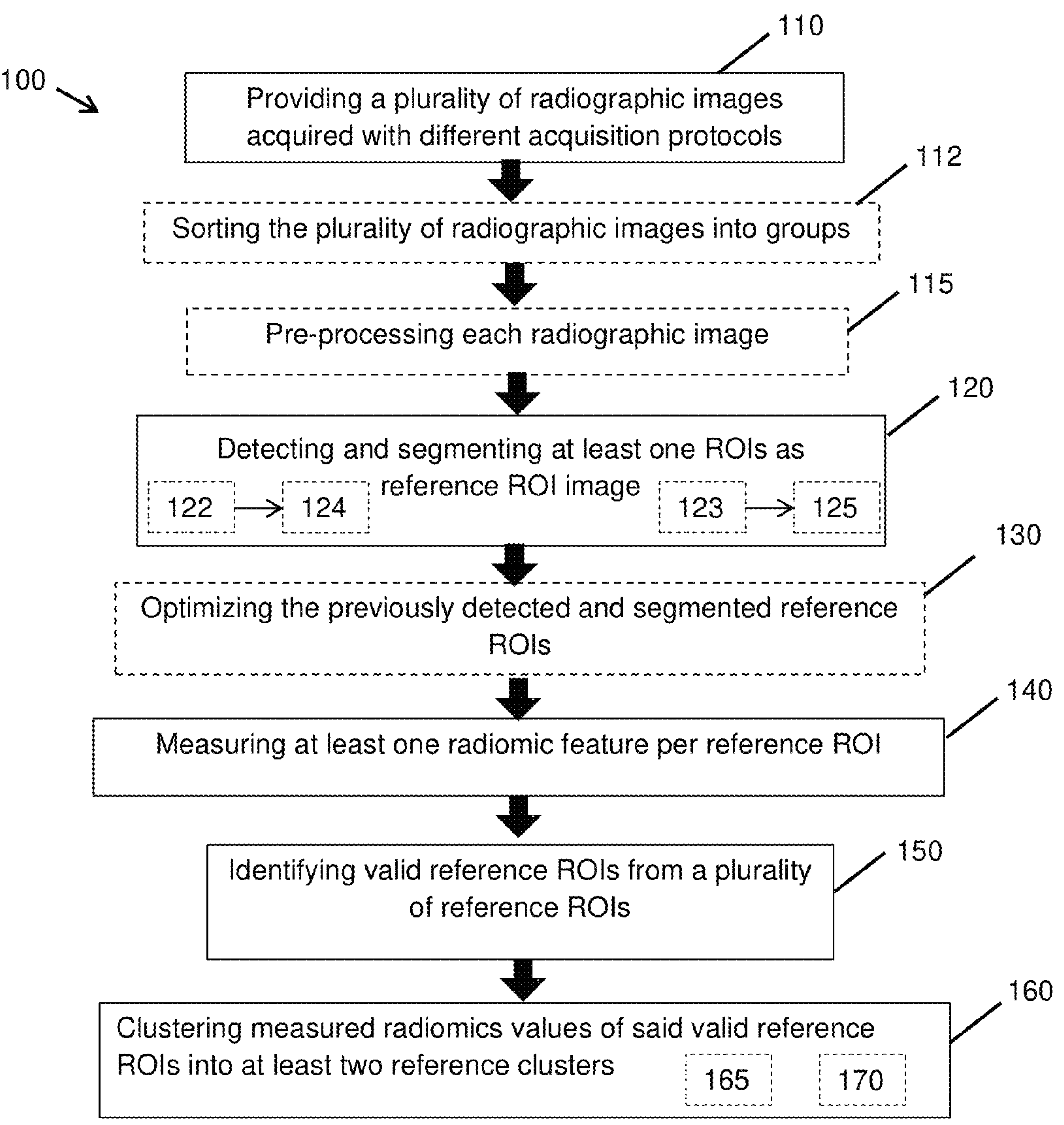
FIG. 1 is a flowchart according to some examples of the method according to the first aspect of the present disclosure.

In order to enhance the reliability of the evaluation-based diagnostic, some proposals have been made to help controlling the impact of the variety of acquisition protocols on the image.

It is disclosed in U.S. patent Ser. No. 10/719,931 titled "Methods and systems for assessing image quality in modeling of patient anatomic or blood flow characteristics" to detect images of suboptimal quality based on the DICOM tags recorded in the header of the images by the scanner. However, the lack of comprehensive and consistent DICOM tags information from the scanner manufacturer and the fact that various DICOM tags combination may lead to a conclusion of similar image acquisition shows that DICOM tags cannot satisfy the need of controlling the impact of image acquisition.

It is recommended by some groups like the Quantitative Imaging Biomarker Alliance (QIBA) to constrain some parameters of the acquisition protocols. This way, images having closer acquisition characteristics can be obtained by accommodating the constraints to imaging centers. However, one difficulty with this proposal is to determine the optimal set of acquisition parameters for a specific application or system. A further difficulty is to adopt the optimal set of acquisition parameters at certain institutions even after those parameters been known and defined for a given application.

It is proposed by Ziegel Mayer et al. (Invest Radiol 2021) to adopt medical imaging technologies like Convolutional Neural Network (CNN), which are supposed to be robust to the variations of acquisition parameters. However, these technologies are costly as they generally require a large amount of training data. Moreover, the robustness of those technologies with respect to variations of acquisition parameters cannot be guaranteed, thus the external validity of the performance of such robustness is often questionable.

Thus, it is desirable to provide a method and system that can address the need of controlling the impact of image acquisition such as the variability in evaluations due to the variety of acquisition parameters without having prior knowledge of the acquisition protocols.

The here proposed disclosure intends to take advantage of this variability in order to control the impact of image acquisition by classifying it. Furthermore, the present disclosure proposes to perform specific measurements that can reflect the variability induced by the variety of acquisition parameters.

The present disclosure proposes to group together images featuring similar characteristics of image acquisition without having prior knowledge of their acquisition protocols.

The present disclosure proposes performing the measurements on each image of a plurality of radiographic images acquired with various acquisition protocols, and automatically grouping the images outputting similar measurements which are likely to have similar characteristics of image acquisition. In the context of the present disclosure, the grouping of images is implemented automatically by generating a machine learning model for automatic classification of radiographic images being acquired by various acquisition protocols, thus achieving at least two reference clusters based on measured values e.g. a set of characteristics of image acquisition.

Further, the present disclosure proposes comparing the measurements performed on a candidate image with those of each of the reference clusters, the candidate image can be classified as associated with the cluster(s) having similar measurements. In the context of the present disclosure, the classification of the candidate image is implemented by applying a machine learning model generated for automatic classification of radiographic images being acquired by various acquisition protocols.

In the field of medicine, radiomics is a method that extracts a large number of features from medical images using data-characterization algorithms. Recent developments in radiomics imaging allow a large amount of measurements to be extracted from images. The radiomics studies show that some of these measurements are variable depending on the image acquisition protocols used. Some of these measurements are even proved particularly sensitive to a slight change of acquisition parameter values. Measurement sensitivity can therefore be used to detect little variations in acquisition parameter values or multivariable changes in the acquisitions.

Furthermore, the present disclosure proposes taking advantages of the variability which is generated by the variety of acquisition protocols.

It is to be noted that in the context of the present disclosure an acquisition protocol is a list of acquisition parameters available on an acquisition machine that are defined to be optimal for given applications.

Further, it is to be noted that in the context of the present disclosure an acquisition modality is the technology enabled to acquire the images. For instance, computed tomography (CT) uses Xray, MRI uses magnetic field and radio pulses, PET uses radioactive tracer captured by gamma camera and so on.

It will be appreciated that the method and system of the present disclosure is applicable to any existing medical imaging modality, and is applicable by extension to any acquisition modality that may be coined in the future. It will be further appreciated that the method and system of the present disclosure is applicable to the association of the already known acquisition modalities such as PET/MRI, shearwave elastography and so on.

Given a determined acquisition modality for example CT modality, the acquisition protocols may involve acquisition parameters being available (or not) on the acquisition machines of different manufacturers. Further, the acquisition protocols may specify acquisition parameters values applicable to different tests. For example, for lung screening program, thin slice, low dose and “lung” reconstruction filters may be recommended. Such a configuration may depend on the test requirements such as to resolve very small nodules, limiting irradiation for annual visit and to optimize contrast in the lung to improve sensitivity/specificity.

The acquisition parameters may be derived from the source (e.g. voltage, current), image sampling (e.g. slice thickness, voxel size), reconstruction technology (e.g. filter Back Projection, iterative software), filtering or distortions. As there are many acquisition parameters and so, even much acquisition parameter values that can be combined. Where every single combination of the acquisition parameter values corresponds to an acquisition protocol, this leads to a large variety of acquisition protocols.

Figure 2:
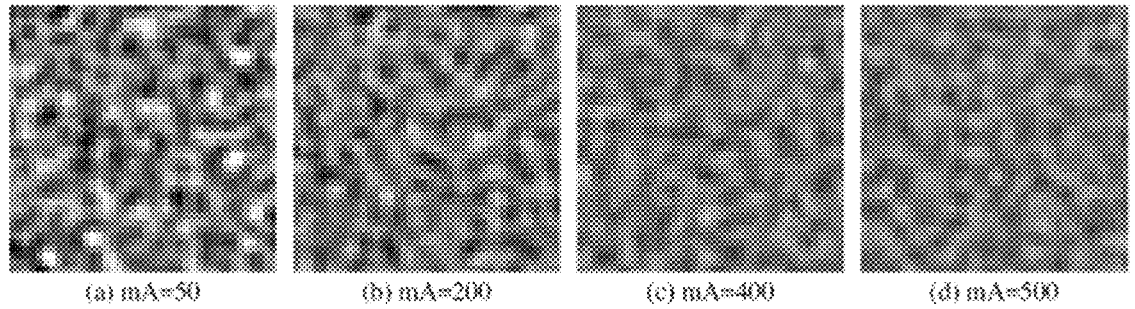
FIG. 2 illustrates an example of impact of variations of the acquisition source current (in mA) on CT images.

FIG. 2 illustrates an example of the impact of the variation on a sample of images acquired by CT modality in function of the source current (mA), this latter being an exemplary acquisition parameter for this acquisition modality. It can be seen from FIG. 2 that the variation (increasing from left to right) of mA has an impact on the characteristics of an image, therefore would have an impact on the value of the radiomic features. In this example, the measurements of the radiomic features may allow to classify images according the different current values (in mA).

It is to be appreciated that the example given above based on the radiomic features is only for illustrative purpose. The present disclosure may extend to other image assessment techniques using features other than radiomic features. In some examples, deep radiomics features may be used for measurements. Corresponding calculations and related steps may vary depending on the features being used for measurements.

The characteristics of image acquisition are image-derived metrics. For example, the characteristics may relate to signal processing such as cut off frequency, signal to noise ratio, low and high frequency energy, auto-correlation of the noise and so on.

In the context of the present disclosure, the characteristics of the image acquisition may relate to the image quality, but is applicable by extension to other types of characteristics of the image acquisition.

In order to take advantage of the variability, the present disclosure proposes to perform measurements in the radiographic images in such a way that the variability of the radiomics measurements would be limited mainly due to variations in the acquisition protocols, rather than other factors such as the anatomical or clinical variations. In some examples, the variability of the radiomics measurements may be limited only to the one due to variations in the acquisition protocols. Notably, patient pathology which may be identified as anatomical variations during imaging investigations may be excluded from analyzing variations in the acquisition protocols.

The present disclosure proposes using regions of interest (ROIs), and in particular detecting and segmenting reference ROIs, where the variability of radiomic measurements is essentially due to variations in the acquisition protocols, to perform the measurements.

In some cases, the radiographic image is an anatomic image, also referred to as clinical image, meaning that it is acquired by imaging only patient.

In a clinical image, several anatomic structures of interest (ASIs) may be shown, such as liver, spleen, lung, muscle and/or soft tissue, bone and so on.

Advantageously, the present disclosure proposes dividing the step of segmenting and detecting at least one ROI as reference ROI by first segmenting non-pathological ASIs and then by segmenting and detecting ROIs in the segmented ASIs. It is to be noted that to be considered as a reference ROI, only non-pathological ROIs under scrutiny are segmented and detected, in other words, ROIs which are “healthy” or “normal” as much as possible. In the context of the present disclosure, the terms “healthy”, “normal” and “non-pathological” have the same meaning and can be interchangeably used. This a manner to ensure that any patient pathology identifiable as anatomical variations during imaging investigations are excluded from the reasons of variability of the radiomics measurements performed on the ROIs selected as reference ROIs.

In some other cases where the radiographic image is a phantom image or a mixed image of a patient in proximity to a phantom object, the ROI will be set on a phantom. In a phantom image or a mixed image, there are phantom-derived structures of interest (PDSIs).

Advantageously, the present disclosure proposes dividing the step of segmenting and detecting at least one ROI as reference ROI by first segmenting PDSIs and then by segmenting and detecting ROIs in the segmented PDSIs.

It will be appreciated that the “reference ROIs” as proposed by the present disclosure should not be limited to any specific examples given herein and can extend to other reference ROIs if the present approach generalize to other aimed indication or acquisition modality.

In one example, Vlieger et al. (JCAT, 2002) selects the reference ROI in the level of the inter-vertebral disk, being compared to the intensity measured in the vertebral bone marrow to generate the so-called Vertebra to Disk Ratio (VDR) biomarker using MRI, with the aim at detecting Gaucher’s disease.

In a further example, Irfan Zeb et al. (Acad. Rad., 2012) considers reference ROI in the level of the spleen in CT, being compared to the attenuation of the liver, with the aim at detecting steatosis.

Advantageously, the present disclosure proposes applying, on reference ROI(s), quality control in order to ensure the appropriateness of considering ROI(s) as reference. The quality control is applied by identifying valid reference ROIs from reference ROIs, where the radiomics values have to fall into predetermined ranges of values for reliable reference ROIs.

Following the above explanations, the present disclosure assumes that radiomic measurements carried out in such valid reference ROIs may produce similar values for images of different patients but acquired by the same acquisition protocol. Based on this principle, for a plurality of images acquired with different protocols, the values of the radiomic measurements can be grouped in clusters and each cluster can then be identified and annotated as relating to a set of characteristics of image acquisition.

The present disclosure may yield significant advantages in data science by redefining the composition of imaging data sets for the training of machine learning models through the identification of homogeneous subsets of imaging data with the aim of improving machine learning algorithmic performance.

According to the present disclosure, the term "scan" is a procedure that provides radiographic images issued from at least one medical imaging technique. At least one of the following two medical imaging acquisition techniques or modalities is particularly foreseen to be used in the framework of the present disclosure:

1) Computed Tomography (CT) scanning of a patient with and without a contrast agent injected prior to the scanning and
2) Magnetic resonance imaging (MRI), with or without a contrast agent injected prior to the scanning, together with Magnetic Resonance Elastography (MRE).

A non-contrasted radiographic image is generated without injecting a contrast agent to the patient prior to the scanning. A contrasted radiographic image is generated with injecting a contrast agent to the patient prior to the scanning. The contrast agent may be designed to highlight specific areas to make at least one chosen among blood vessels, organs and tissues more visible during a scanning, and potentially at different determined times after the injection. Thus, a contrasted radiographic image may for instance aim at highlighting the arterial phase during a first scanning step, and the portal venous phase during a second scanning step, by using the same contrast agent at different determined times after the injection or by using different contrast agents. Another phase might be observed during a scan according to the present disclosure that is called delayed phase because the corresponding scanning step is delayed, with a determined period of time, with respect to at least one among the first and second scanning steps as introduced above. Such a scanning of the delayed phase can allow highlighting other specific areas to make other features more prominent with respect to arterial and/or portal venous phases. Delayed phase acquisition during a further scanning step of a scan according to the present disclosure can follow either acquisition of the arterial phase and/or acquisition of the portal venous phase.

A scan according to the present disclosure may comprise a series of scanning steps made by implementing at least once one of the two above mentioned medical imaging techniques in order to provide radiographic images of interest.

According to the present disclosure, the term "machine learning" refers to computer algorithm(s) able to automatically make classification(s) without explicit programming. The computer algorithm builds said mathematical model from training data.

According to the present disclosure, the term "unsupervised classification" refers to classification without providing sample classes (labels).

The term "clinical ground truth" or "clinical metadata" refers to data about a patient which have been acquired by physical examination, medical examination, or clinical examination. It may comprise at least one among: age, sex, height, weight, BMI, ethnic origin, medical conditions, risk factors, nodule size, IO response (for instance low or high value), treatment type, and tumor type of each patient.

Example embodiments will now be described, including method and system for generating a machine learning model for automatic classification of radiographic images, and for classifying at least one radiographic images by applying a machine learning model generated for automatic classification of radiographic images.

FIG. 1 shows a flowchart according to some examples of the method according to the first aspect of the present disclosure.

With reference to FIG. 1, a method 100 is shown for generating a machine learning model for automatic classification of radiographic images acquired by various acquisition protocols.

As shown in FIG. 1, the method 100 comprises a step 110 of providing a plurality of radiographic images of at least two different patients.

According to some examples, the radiographic images of each of the at least two different patients are acquired with acquisition protocols different from each other.

According to one example, there are at least a first patient and a second patient. Where the acquisition modality is a single modality, e.g. CT modality being applied to both of the first patient and the second patient, the radiographic images of the first patient and of the second patient may be acquired by different acquisition protocols.

It will be appreciated that the method of the present disclosure is applicable to any existing medical imaging modality such as CT, MRI, PET and so on, and is applicable by extension to any acquisition modality that may be coined in the future. It will be further appreciated that the method of the present disclosure is applicable to the association of the already known acquisition modalities such as PET/MRI, shearwave elastography and so on.

It will be appreciated that in the context of the present disclosure, a radiographic image may be one among the non-contrasted phase, the arterial phase, the portal venous phase and the delayed phase.

Figure 3A:
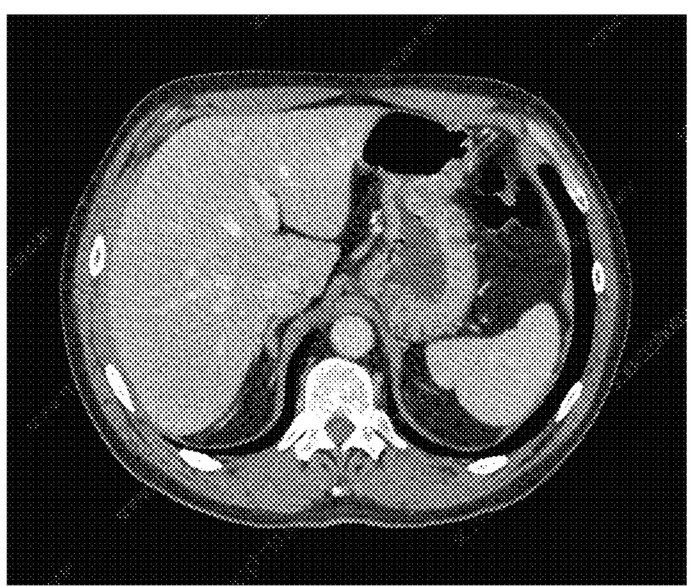
FIGS. 3*a* to 3*c* show respectively three kinds of radiographic image namely clinical image, phantom image and mixed image, respectively.
Figure 3B:
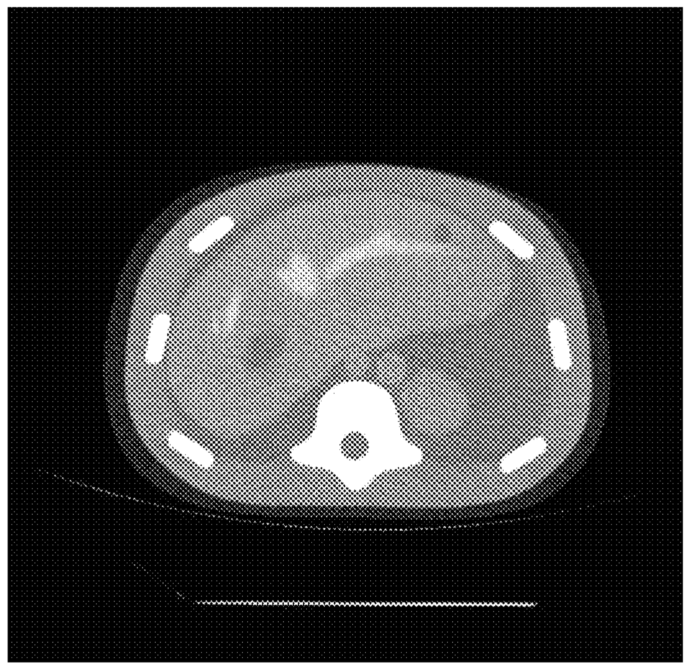
Figure 3C:
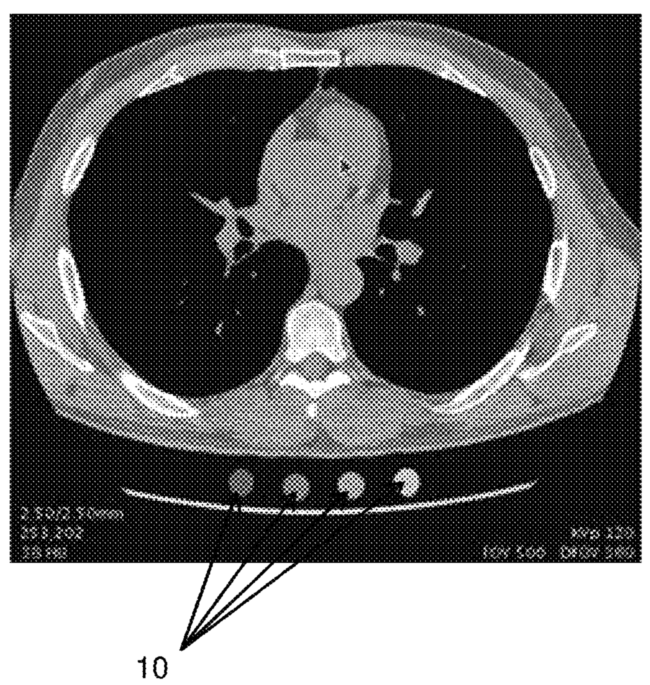

FIGS. 3*a*-3*c* show three kinds of radiographic image. FIG. 3*a* is a clinical image being acquired by imaging a patient. FIG. 3*b* is a phantom image being acquired by imaging a phantom object, more precisely a CT scan of an anthropomorphic abdominal phantom. FIG. 3*c* is a mixed image combining a patient and a pocket phantom being acquired by imaging the patient with the phantom object in proximity to the patient. In FIG. 3*c*, the pocket phantom is made of four spheres 10 of different materials.

It will be appreciated that in the context of the present disclosure, the number of the phantom object is not limited and can be any integral number equal to or larger than one.

It will be appreciated that in the context of the present disclosure, "in proximity to" means that the distance between a patient and a pocket phantom depends on the modalities being considered as well as the respective imaging properties. Some examples are given in the article titled "How reliable are ADC measurements? A phantom and clinical study of cervical lymph nodes" by Moreau B. et al., Eur Radiol. 2018 August, and in the article titled "Non-Stationary CT Image Noise Spectrum Analysis" by Balda et al. published in 2010.

In some examples, the pocket phantom is disposed above the patient, with or without contact with the latter. In some examples, the phantom object is situated next to the patient. It is to be noted that in the context of the present disclosure, the relative position of the patient and the phantom object is not limited to the examples given here.

According to an example of the present disclosure, the radiographic images comprise more than one kind among the clinical, phantom and mixed images. According to another example of the present disclosure, the radiographic images comprise only one kind among the clinical, phantom and mixed image.

As shown in FIG. 1, the method 100 may further comprise, after the step 110 of providing the radiographic images, a step 112 of sorting the plurality of radiographic images into a first group and a second group. The optional aspect of this step 112 is depicted on FIG. 1 by the fact that the concerned block is in dashes.

In some examples, the first group of radiographic images comprises clinical images and the second group of radiographic images comprises phantom images and/or mixed images each combining a patient and a pocket phantom. Preferably, in the first group, there are only clinical images. Also preferably, in the second group, there is at least a phantom object as being imaged in the phantom images and/or mixed images.

In some examples, there is at least one image in the first group or the second group.

In some examples, the sorting of the plurality of radiographic images may be performed by tagging each of the radiographic images. In still some examples, the tagged images may be stored in a local storage and/or in a cloud storage.

In some examples, the first group of the plurality of radiographic images is used to generate a first machine learning model and the second group of the plurality of radiographic images is used to generate a second machine learning model.

In the context of the present disclosure, the first machine learning model being generated with clinical images may be referred to as a clinical machine learning model, and the second machine learning model being generated with phantom images and/or mixed images may be referred to as a phantom machine learning model.

Figure 5:
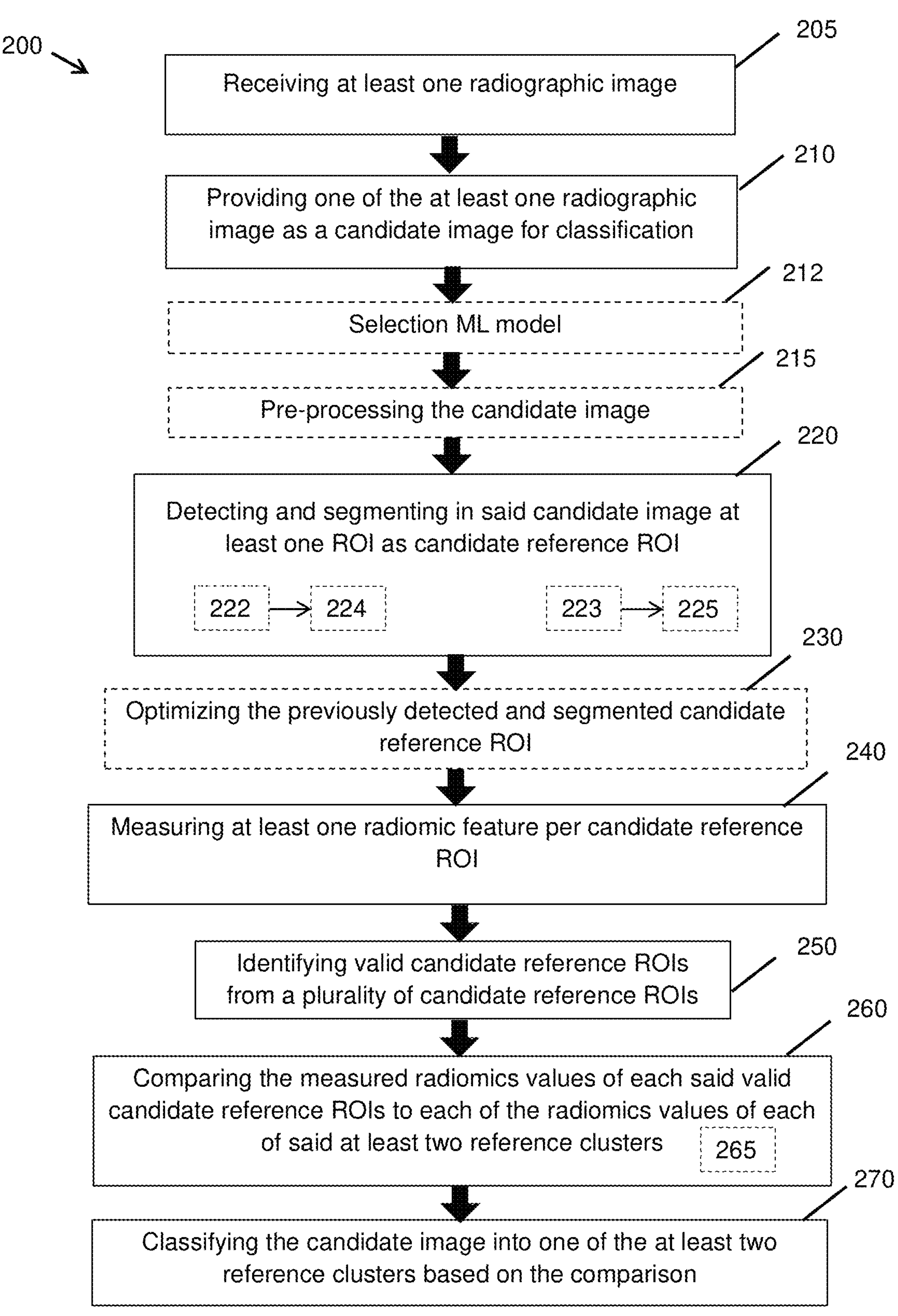
FIG. 5 is a flowchart according to some examples of the method of the second aspect of the present disclosure.

As illustrated, the method 100 may further comprise a step 115 of pre-processing each of the plurality of radiographic image. The optional aspect of this step is depicted on FIG. 1 by the fact that the concerned block is in dashes. Note that the same applies to step 130 as illustrated in FIG. 1 and to steps 215 and 230 as illustrated in FIG. 5.

In some examples, said pre-processing 115 is performed by using at least one of the following image processing technique: denoising, resampling, diffusion-weighted magnetic resonance imaging and apparent diffusion coefficient mapping. It will be appreciated that in the context of the present disclosure, the pre-processing is not limited to the above image processing techniques.

In the context of the present disclosure, the denoising allows to improve the quality of the image. Further, the resampling ensures that all images will be computed in the same way thus making the image having the same or similar geometry, which will help in the assessment of textures in images, particularly for computing co-occurrence matrix and Haralick texture features. Improving the texture feature assessments can improve radiomics measurements accordingly.

As shown in FIG. 1, the step 115 of pre-processing is performed prior to the step 120 of detecting and segmenting in each of said radiographic images at least one region of interest (ROI) as reference ROI which will be described below.

Accordingly, the pre-processing step 115 allows to improve the subsequent separation of clusters and to help detect artifacts by enhancing the quality of the different segmentations (ASI and ROI) and that of the radiomics features.

It is to be noted that although in FIG. 1 it is illustrated that the step 115 is after the step 112, in the context of the present disclosure, this step 115 may be performed either before or after the step 212 of sorting the plurality of radiographic images.

Said radiographic images as further processed in accordance with the steps of the method 100 as described below may thus stand for raw images or pre-processed radiographic images as well.

Still referring to FIG. 1, the method 100 further comprises a step 120 consisting in defining and segmenting in each of the radiographic images at least one region of interest (ROI) as reference ROI.

In some examples, where the radiographic images are clinical images which correspond to the first group of radiographic images, the step 120 may comprise detecting and segmenting in each clinical image at least one non-pathological region of interest (ROI) as reference ROI.

In some examples, the step 120 of detecting and segmenting non-pathological ROIs may be achieved by first segmenting various non-pathological anatomical structure of interest (ASIs) (substep 122), and then segmenting and detecting ROIs in the already segmented ASIs (substep 124).

Figure 4A:
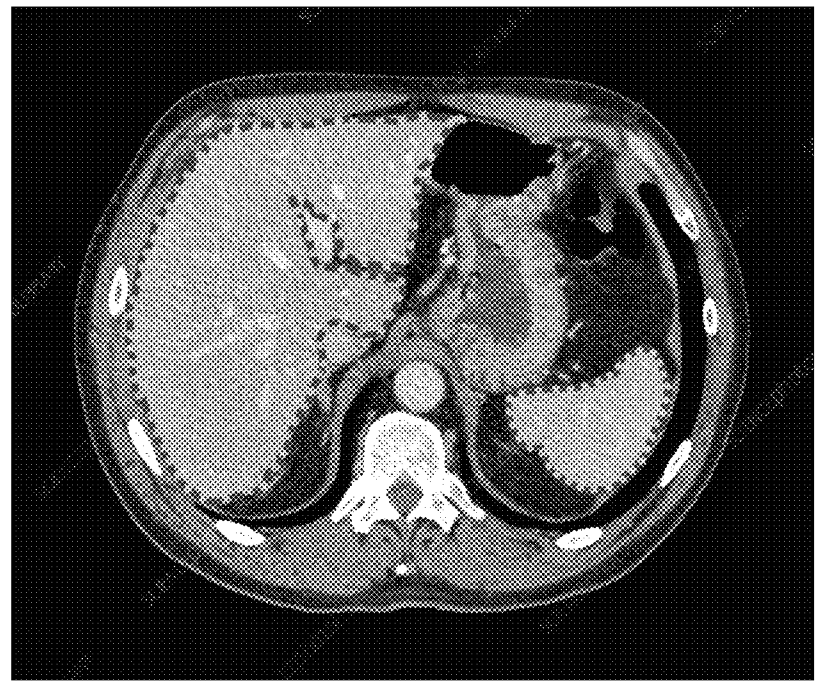
FIG. 4*a* shows two segmented anatomical structures of interest (ASIs), each defined by a dash contour.

As shown in FIG. 4*a*, two organs (as ASIs) are segmented namely liver and spleen (indicated by dashed lines). At the same time, a set of segmentation masks of ASIs may be generated.

In some examples, the substep 122 of segmenting non-pathological ASIs may comprise, prior to segmenting ASIs, detecting the coordinates of various ASIs.

The substep 122 may further comprise, following segmenting ASIs, performing a series of tests on the segmented ASIs to select the non-pathological ASIs in order to ensure that only the non-pathological ASIs will be retained and used for the following steps.

The tests performed for selecting non-pathological ASIs may be for example a test to obtain the size of an ASI, a check on the patients' record related to the ASI in question or any factor that may be relevant to the pathological status of an ASI.

It will be appreciated that the non-pathological ASIs may be detected by either humans (for example a radiologist) or by artificial intelligence, the method according to the present disclosure is applicable to either case.

It will be appreciated that in the context of the present invention, an ASI may be any anatomical structure, such as an organ: liver, spleen, lung, or muscle, or soft tissue, or bone. It is to be noted that the present invention does not limit the ASI to the listed examples. In the context of the present disclosure, an ASI refers to the entire part of each anatomic structure. An example of an entire organ may be a whole liver.

Figure 4B:
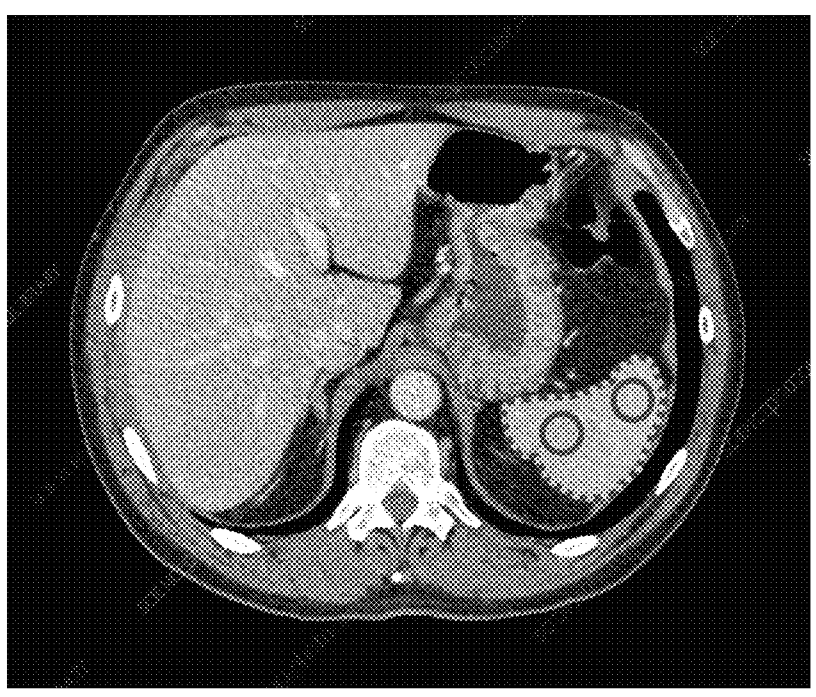
FIG. 4*b-c* show respectively two-three segmented and detected non-pathological ROIs in one of the two segmented ASIs illustrated on FIG. 4*a*, each non-pathological ROI being defined by solid circle, according to some examples of the present disclosure.
Figure 4C:
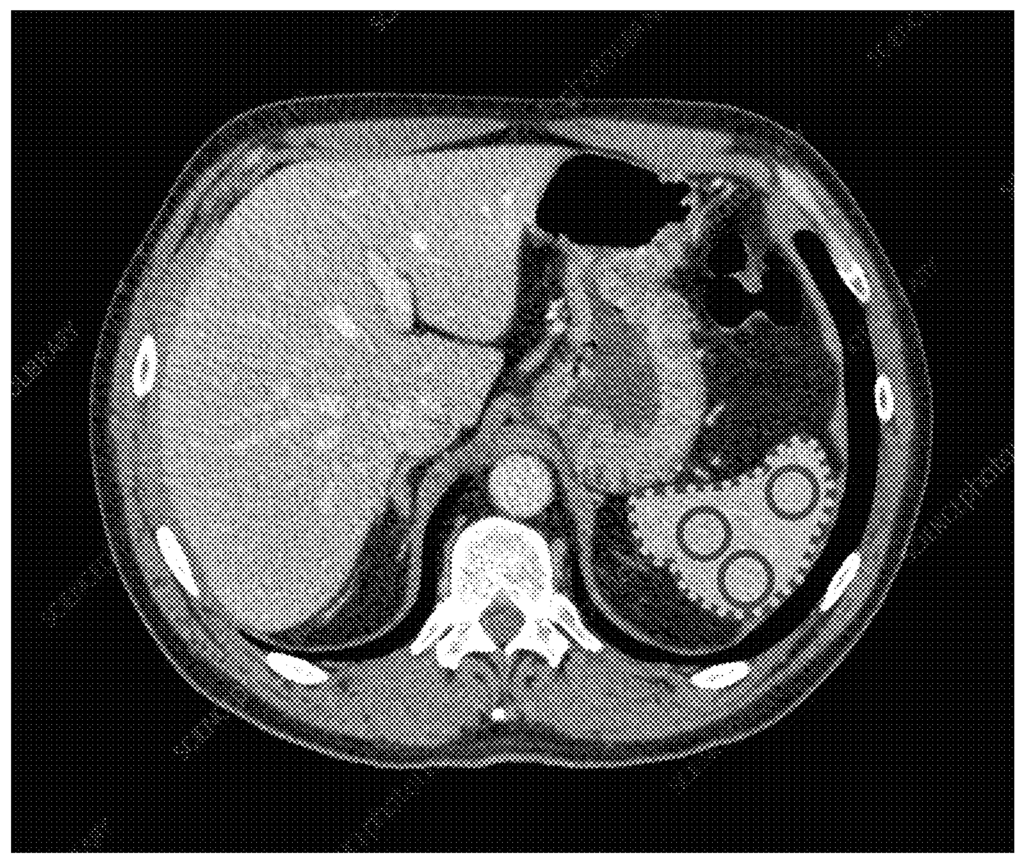

In the example of FIG. 4*b*, two ROIs are segmented and detected (indicated by solid circles), inside the segmented spleen (indicated by dashed line contour). In the example of FIG. 4*c*, three non-pathological ROIs are segmented and detected (indicated by solid circles), inside the segmented spleen (indicated by dashed line contour).

It is assumed, in the context of the present disclosure, that the ASIs as shown in FIG. 4*b* and FIG. 4*c* are non-pathological ASIs.

It will be appreciated that although the present disclosure describes detecting and segmenting in each clinical image at least one non-pathological ROI by first segmenting non-pathological ASIs, then segmenting ROIs inside the non-pathological ASIs, other means being configured to obtain non-pathological ROIs may be possible.

For example, non-pathological ROIs may be obtained directly in the clinical image without segmenting ASIs.

Further, for instance, clinical metadata records may have been generated from clinical ground truth acquired by physical examination, medical examination, or clinical examination. Such clinical metadata records may be used to ascertain that the ROIs selected as reference ROIs are related to a healthy, or normal, body part.

It will be appreciated that according to the present disclosure, the overall number of reference ROIs being detected and segmented in the segmented non-pathological ASIs is not limited to two and three as shown in FIG. 4*b* and FIG. 4*c* and may be any integer equal to or larger than 1.

As shown in FIG. 4*a* at the step 122 of segmenting ASIs, a set of segmentation masks of ASIs may be generated, being applied to, for example, the spleen and the liver, following localizing ASIs in each of the radiographic image. Generally speaking, the image segmentation allows to partition image into disjoint regions with voxels and/or pixels in the same region having high similarity and pixels in different regions having low similarity. A mask per ASI may be generated as the output of the image segmentation process 120.

Advantageously, for a given first group of radiographic images taken during a same scanning step, the same set of segmentation masks of ASIs can be reused during the search or detecting and segmenting of ROIs, thus reducing the related computing and storage resources.

In some further examples, where the radiographic images are either phantom images and/or mixed images each combining a patient and a pocket phantom, in other words, comprising at least a phantom object, and which images correspond to the second group of radiographic images, the step 120 may comprise firstly segmenting various phantom-derived structure of interest (PDSIs) (substep 123) based on a reference material, and then segmenting and detecting ROIs in the already segmented PDSIs (substep 125).

It will be further appreciated that according to the present disclosure, the number of reference ROIs detected and segmented in all segmented PDSIs may be any integer equal to or larger than 1.

In the context of the present disclosure, PDSI refers to the entire phantom-derived structure.

In a preferred example, the reference material is chosen to approach the maximum imitation of the human tissue. Some examples are explained in the article titled "Intra-scan inter-tissue variability can help harmonize radiomics features in CT" by Beaumont H. et al., Eur Radiol. 2021 Aug. 6. and Eur Radiol. 2021 Sep. 24. In some examples, the phantom may be made of 10 layers of different materials: A: Plaster resin; B: Natural Cork; C: Solid Acrylic; D: Dense Cork; E: Rubber Particles; F: Sycamore Wood; G: 50% Filled Acrylonitrile Butadiene Styrene (ABS); H: 40% Filled ABS; I: 30% Filled ABS; J: 20% Filled ABS. It will be appreciated that the present disclosure is not limited to the number of layers and the materials being used as described here.

Advantageously, the step of segmenting PDSIs may generate a set of segmentation masks of PDSIs, following localizing PDSIs in each of the radiographic image. For instance, for a given second group of radiographic images taken during a same scanning step, the same set of segmentation masks of PDSIs can be used to further detect and segment the ROIs, thus reducing the related computing and storage resources.

It is to be noted that, for the second group of radiographic images, as they comprise at least a phantom object for which the pathological status is not relevant, the detecting and segmenting ROIs may not be related to the pathological status of the phantom-derived structures.

As illustrated, the method 100 may further comprise a step 130 of optimizing at least one of the previously defined and segmented reference ROIs, after the step of detecting and segmenting 120 at least one region of interest (ROI) as reference ROI. This step 130 may be performed by implementing at least one image processing technique chosen among data binning and rescaling. The step 130 may more particularly be applied over the segmentation mask region associated to the radiographic image under consideration.

Advantageously, optimizing the reference ROIs by binning and/or rescaling may improve computing the co-occurrence matrix in the following steps.

As previously mentioned, it may be advantageous to consider radiomic measurements as measured on different reference ROIs where the variability is mainly, or even solely, due to variations in the acquisition protocol, rather than due to any anatomical or clinical variations.

In one example referring to the above paragraph, it allows to select the reference ROI in the same ASI, thus providing more robust measurements.

Indeed, it turns out that the modification of the acquisition protocols not only makes variable the value of the radiomics, but also the difference between the radiomics values between two tissues in the same image. However, some systems are more interesting in detecting significant differences between two tissues in the same image rather than the absolute value of one of these tissues.

In another example following the above paragraph, where clinical images are concerned, it is proposed to perform several measurements in each of the given ASIs. In this example, a first reference ROI of patient is related to the spleen and a second reference ROI of patient is related to the liver. Thus, the combination of the same radiomic features extracted from these two non-pathological reference ROIs, coming from two ASIs of different nature may be used to study the acquisition-characteristic-based classification. It is to be noted that in the context of the present disclosure, an example of ASIs of the same nature may be the left and the right kidneys, or Psoas muscles. It is to be understood that ASIs of different nature means the ASIs are not of the same nature. By saying the "same radiomic features", it is meant that the same mathematical computing is performed. In one example, the entropy according to the Haralicks' definition is used as the radiomics feature. With regard to "intra-scan inter-tissue evaluation", the term "tissue" may be understood as interchangeable to "ASI".

The method 100 further comprises a step 140 of measuring at least one radiomic feature per reference ROI.

In some examples, the step 140 may for instance be implemented by radiomics computing of each reference ROI. Preferably, the computing tools used for radiomics computing may be one of the following computing tools or any combination thereof: histograms, joint distributions and frequency analysis. It will be appreciated that other computing tools designed for the same or a different family of radiomics may also be used in the context of the present disclosure.

Advantageously, the present disclosure proposes applying on reference ROI quality control in order to ensure the appropriateness of considering ROI as reference.

In order to achieve this, as illustrated, the method 100 may further comprise a step of identifying 150 valid reference ROIs from a plurality of reference ROIs based on the measured radiomics feature.

In some examples, the step 150 may further comprises comparing the measured radiomics values to a predetermined range of radiomics values preferably chosen from a set of reference value ranges and determining a valid reference ROIs if the measured radiomics values thereof fall into said predetermined range of radiomics values.

In some examples, the set of reference value ranges may comprise at least one reference value range, where each reference value range corresponds to a specific value range being acquired with a particular acquisition modality and for a particular ASI.

Preferably, the value range is measured in HU (Hounsfield Unit). In some examples, the value range may be measured in other metrics of density. In some other examples, the value range may correspond to other metrics such as the volume of a given organ and be measured by a metric of geometry. It will be appreciated that the value range is not limited to the examples listed above and may extend to any metrics suitable for measurements according to any method of the present disclosure.

In one example, where the acquisition modality is CT, the reference parameter for spleen is for instance splenic attenuation and may approximately range from 35 to 55 HU.

For non-limitative examples, the mean attenuation reference range in CT as the exemplary acquisition modality is substantially:

For non-spleen diseased patients, 35-55 HU (for splenic attenuation),

For non-muscular diseased patients, 20 to 40 HU (for muscle tissues), and

For phantom reference, 10 to 100 HU (when measuring acrylic).

Such comparison may allow making sure that a reference ROI is valid if for example, the segmented ASI of the reference ROI does not include any unwanted anatomical structures. According to some examples of the present disclosure, the unwanted anatomical structures may be veins, arteries, inflammation and so on. By identifying the valid reference ROIs, it ensures that only reference ROIs not including the unwanted anatomical clinical structures will be retained and used for the following steps.

Advantageously, the step 150 allows applying the quality control regarding the appropriateness of the reference ROIs to identify valid reference ROIs, thus improving the following classification using the measured radiomics values of only the valid reference ROIs.

Always by referring to FIG. 1, the method 100 further comprises a step 160 of clustering the measured radiomics values of the valid reference ROIs into at least two reference clusters according to a set of characteristics of image acquisition.

This step 160 thus results in grouping the performed measurements by similarity into reference groups called clusters.

In the context of the present disclosure, this may be advantageously achieved by unsupervised classification, in other words, grouping together images featuring similar characteristics of image acquisition without having prior knowledge of their acquisition protocols.

In some examples, the step 160 may comprise a step 165 of classifying the measurements of valid reference ROIs into at least two clusters. In some further examples, the step of classifying 165 may be implemented by using at least one data clustering technique chosen among K-means clustering or DBScan (density-based spatial clustering of applications with noise) clustering or Agglomerative Hierarchical clustering or Expectation-Maximization with GMM (Gaussian Mixture Models) clustering. It will be appreciated that the present disclosure is not limited to the above listed clustering techniques.

In some examples, the step 160 of clustering may further comprises a step 170 of characterizing the at least two clusters in order to obtain at least two reference clusters. In some examples, the step 170 may comprises labeling cluster centroid or the bounding limits of clusters.

It is thus achieved a list of labeled clusters. Each cluster is thus identified and annotated, or labeled, as according to a set of characteristics of image acquisition.

FIG. 5 shows a flowchart according to some examples of the method of the second aspect of the present disclosure, that is, a method for classifying at least one radiographic image by applying a machine learning model.

According to the embodiment illustrated on FIG. 5, the present disclosure provides a method 200 for classifying at least one radiographic image according to a set of characteristics of image acquisition by applying a machine learning model defining at least two reference clusters of radiographic images. Said learning model may have been generated by implementing the method 100 according to any embodiment of the first aspect of the disclosure.

Firstly, the method 200 comprises a step 205 of receiving at least one radiographic image. Then, the method 200 may comprise a step 210 of providing one of the at least one radiographic image as a candidate image for classification.

It is to be noted that "at least one" radiographic image refers to the number of radiographic images and does neither refer to nor limit the number of patients. It is to be understood that the at least one radiographic image may be of the same patient or of different patients.

As explained previously with reference to the embodiments according to method 100, the at least one radiographic image may comprise at least one kind of the following: clinical image acquired by imaging a patient, phantom image acquired by imaging a phantom object, and mixed image each comprising a patient and a pocket phantom acquired by imaging a patient with a phantom object in proximity to the patient.

It is to be noted that in the context of the present disclosure, description made previously to the embodiment of method 100 should be applicable to the embodiment of method 200.

As shown in FIG. 5, the method 200 may further comprise, before the step 220 of detecting and segmenting and after the step 210 of providing one of the at least one radiographic image as a candidate image for classification, a step 212 of selecting a machine learning (ML) model to be applied based on the candidate image for classification. In some examples, a specific group of clusters is thus selected.

In some examples, selecting 212 a machine learning model to be applied for classification may comprise the following substeps:

determining that the machine learning model to be applied is the first machine learning model having been generated with clinical images if the candidate image is a clinical image;

determining that the machine learning model to be applied is the second machine learning model having been generated with phantom images and/or mixed images if the candidate image is an image of a phantom object or a mixed image of a patient with a pocket phantom.

In some examples, selecting 212 a machine learning model may be implemented by selecting a specific group of clusters based on the kind of the candidate image. Following this, the selected group of clusters may be used for classification.

Advantageously, the present disclosure allows to automatically detect for each candidate image the kind of image and then to associate each candidate image with the corresponding model. In one example, the corresponding model refers to a set of clusters. In a preferred embodiment, the automatic detection is performed based on the kind of the candidate image.

In some examples, a specific kind of image is received, in doing so, the model to be applied may have been known given the kind of image, even before providing the image as a candidate image. In this example, it can be assumed that it has been determined which machine learning model is to be applied before providing the image as a candidate image. Therefore, the step 212 of selecting a ML model may be unnecessary and therefore may be omitted from the method 200.

A pre-processing step 215, conformed to the above detailed step 115, may be performed before the step 220 of detecting and segmenting at least one ROI as candidate reference ROI. In some examples, the step 215 is performed by using preferably at least one of the following image processing techniques: denoising and resampling, diffusion-weighted magnetic resonance imaging and apparent diffusion coefficient mapping.

It is to be noted that although in FIG. 5 it is illustrated that the step 215 is after the step 212, in the context of the present disclosure, this step 215 may be performed either before or after the step 212 of selecting machine learning model.

Still referring to FIG. 5, the method 200 further comprises a step 220 of detecting and segmenting in the candidate image at least one region of interest (ROI) as candidate reference ROI. The step 220 may be conformed to the step 120 as detailed above.

In some further examples, if it is determined that the machine learning model to be applied is the first machine learning model, step 220 may further comprise detecting and segmenting in the candidate image at least one non-pathological ROI as candidate reference ROI.

As explained above, in some examples, determining which machine learning model to be applied in the method 200 according to the second aspect of the present disclosure may not require the step 212 of selecting the machine learning model based on the candidate image for classification. In one further example, it may be determined by human which machine learning model will be applied. In some other examples, determining which machine learning model is to be applied may require the selecting step 212 before the step 220 of detecting and segmenting.

In some examples, the step 220 may comprise a step 222 of segmenting various non-pathological anatomical structures of interest (ASIs), and a step 224 of segmenting and detecting ROIs in the segmented ASIs as candidate reference ROIs. In some examples, the step 222 further comprises generating a set of segmentation masks of ASIs, and the step 224 further comprises detecting and segmenting ROIs using the set of segmentation masks of ASIs.

On a similar principle, if it is determined that the machine learning model to be applied is the second machine learning model, step 220 may further comprise a step 223 of segmenting various phantom-derived structure of interest (PDSIs), and a step 225 of segmenting and detecting ROIs in the segmented PDSIs. In some examples, the step 223 further comprises generating a set of segmentation masks of PDSIs, and the step 225 further comprises detecting and segmenting ROIs using the set of segmentation masks of PDSIs.

As illustrated, the method 200 may further comprise a step 230 of optimizing at least one of the previously detected and segmented candidate reference ROIs by at least one image processing technique chosen among data binning and rescaling. The step 230 may be conformed to the step 130 as detailed above.

Still referring to FIG. 5, the method 200 may further comprise a step 240 of measuring at least one radiomics feature per candidate reference ROI. The step 240 may be conformed to the step 140 as detailed above.

Preferably, the method 200 may further comprise a step 250 of identifying valid candidate reference ROIs from a plurality of candidate reference ROIs based on the measured radiomics values. The step 250 may be conformed to the step 150 as detailed above.

Still referring to FIG. 5, the method 200 may comprise a step 260 of comparing the measured radiomics values of each of the valid candidate reference ROIs to each of the radiomics value of each of said at least two reference clusters. In one example, the radiomics value of a cluster may be calculated based on the value of the centroid of the cluster.

In some examples, the comparing step 260 may comprise a step 265 of calculating a distances between the measured radiomics values of each of the valid candidate reference ROIs and each of the radiomics values of each of the at least two reference clusters. In some examples, the step 265 may be implemented in accordance with a predetermined metric preferably chosen among: Manhattan metric, Euclidian metric and Minkowski metric. It will be appreciated that, in the context of the present disclosure, the calculation described can also be implemented by other metrics not described here.

As illustrated in FIG. 5, the method 200 further comprises a step 270 of classifying the candidate image into one of the at least two reference clusters based on the comparison.

In some examples, the classifying step 270 may comprise selecting the cluster having the smallest calculated distance and/or eliminating the cluster having the largest calculated distance.

In one example, three candidate reference ROIs have been identified with the measured radiomics values denoted as R1, R2, R3 respectively, and two reference clusters are available with the centroid values denoted as c1 and c2 respectively, leading to six distances being calculated according to, for example, Euclidian distance as D1, D2, D3, D4, D5 and D6. The six distances are referred to as follows:

D1=R1, c1; D2=R1, c2; D3=R2, c1; D4=R2, c2; D5=R3, c1; D6=R3, c2; and among which D2 has the smallest value. For this example, as R1-R3 are located in the same ASI (tissue), for instance, we compare the average distance between the ROI and the centroid.

One way to select the cluster is to consider the minimum distance between one ROI and one cluster. For example, we can keep D2 as the smallest value, allowing selecting cluster 2.

An alternative way is to choose to calculate the average value of the distances that involve each cluster. For example, D2, D4, D6 because they are involved with cluster 2. In the alternative example, the average value of the distances is calculated as follows: (D2+D4+D6)/3.

The technical advantage of proceeding by exclusion, in other words, determining the most distant cluster instead of selecting the closet cluster is that it allows pre-training the models on larger data sets, admittedly less specific model pre-training.

It is thus achieved the automatic classification of the considered radiographic image as being acquired by various acquisition protocol into one of the at least two reference clusters.

Thus, when a candidate image is provided to the machine learning model, at least one ROI is detected and segmented as reference ROI, radiomics measurements are performed per candidate reference ROI and valid candidate reference ROIs are identified based on the measurements, these measurements are then compared to measurements of previously constituted clusters. Comparing the measurements of the candidate image with those of the clusters makes it possible to find the closest measurements and, therefore, to identify the cluster of images similar to the candidate image. The candidate image therefore has a greater probability to have the same characteristics of image acquisition as that used for the images of the corresponding cluster(s).

It is indeed possible that the considered radiographic image be classified into more than one cluster. Nonetheless, by crossing the achieved classification with other information, for instance by crossing with clinical records, it is possible to discriminate between clusters to which the radiographic image to be classified may pertain after step 270.

Thus the comparison of radiomics measurements between the candidate image and the different clusters can be done in different ways. Within each given cluster, the images can be used independently to test the candidate image to be classified, or centroids of mean values can be calculated. Advantageously, the incremental value of these different approaches can be assessed based on the classification performance.

The present disclosure further proposes a computer-implemented system for automatic classification of radiographic images, comprising: at least one machine learning model being generated to classify at least one radiographic image according to a set of characteristics of image acquisition related to image quality.

The embodiments and aspects of the here detailed disclosure may be described and illustrated in conjunction with systems, devices and methods which are meant to be exemplary and illustrative, not limiting in scope. Specific configurations and details may be set forth in order to provide an understanding of the disclosure. However, it should be apparent to one skilled in the art that the disclosure may be practiced without some of the specific details being presented herein. Furthermore, some well-known steps or components may be described only generally, or even omitted, for the sake of illustrative clarity.

Some processes may be presented and described in a series (sequence) of steps. It should be understood that the sequence of steps is exemplary, and that the steps may be performed in a different order than presented, some steps which are described may be omitted, and some additional steps may be omitted from the sequence and may be described elsewhere.

Reference may be made to disclosures of prior patents, publications and applications. Some text and drawings from those sources may be presented herein, but may be modified, edited or commented to blend more smoothly with the disclosure of the present application. Citation or identification of any reference should not be construed as an admission that such reference is available as prior art to the disclosure.

The methods described herein may be implemented on any form of computer or computers. The components thereof may be implemented as dedicated applications or in client-server architectures, including a web-based architecture, and can include functional programs, codes, and code segments. Any of the computers may comprise a processor, a memory for storing program data and executing it, a permanent storage such as a disk drive, a communication port for handling communications with external devices, and user interface devices, including a display, keyboard, mouse, etc. When some software or algorithms are involved, they may be stored as program instructions or computer readable codes executable on the processor on a computer-readable media such as read-only memory (ROM), random-access memory (RAM), CD-ROMs, magnetic tapes, floppy disks, and optical data storage devices. The computer readable recording medium can also be distributed over network coupled computer systems so that the computer readable code is stored and executed in a distributed fashion. This media can be read by the computer, stored in the memory, and executed by the processor.

For the purposes of promoting an understanding of the principles of various embodiments of the disclosure, reference has been made to a preferred embodiment illustrated in the drawings, and specific language has been used to describe this embodiment. However, no limitation of the scope of the disclosure is intended by this specific language, and the disclosure should be construed to encompass all embodiments that would normally occur to one of ordinary skill in the art.

The disclosure may be described in terms of functional block components and various processing steps. Such functional blocks may be realized by any number of hardware and/or software components configured to perform the specified functions. For example, the present disclosure may employ various integrated circuit components, e.g., memory elements, processing elements, logic elements, look-up tables, and the like, which may carry out a variety of functions under the control of one or more microprocessors or other control devices. Similarly, where the elements of the present disclosure are implemented using software programming or software elements the present disclosure may be implemented with any programming or scripting language such as C, C++, Java, assembler, or the like, with the various algorithms being implemented with any combination of data structures, objects, processes, routines or other programming elements. Functional aspects may be implemented in algorithms that execute on one or more processors. Furthermore, the present disclosure could employ any number of conventional techniques for electronics configuration, signal processing and/or control, data processing and the like.

The invention claimed is:

1. A method for generating a machine learning model for automatic classification of radiographic images acquired by various acquisition protocols, comprising:

Providing a plurality of radiographic images of at least two different patients, the radiographic images of each of the at least two different patients being acquired with acquisition protocols different from each other, Detecting and segmenting in each of said radiographic images at least one regions of interest (ROI) as reference ROI, Measuring at least one radiomic feature per reference ROI, Identifying valid reference ROIs from a plurality of reference ROIs based on the measured radiomics values, Clustering the measured radiomics values of said valid reference ROIs into at least two reference clusters according to a set of characteristics of image acquisition, wherein the plurality of radiographic images comprises at least one kind of the following: clinical images being acquired by imaging a patient, phantom images acquired by imaging a phantom object, and mixed images each combining a patient and a pocket phantom acquired by imaging a patient with a phantom object in proximity to the patient, and wherein said clinical images are used to generate a first machine learning model and said phantom images and/or said mixed images are used to generate a second machine learning model.

2. The method according to claim 1, further comprising, before detecting and segmenting at least one ROIs as reference ROI, pre-processing each of said radiographic images by using at least one of the following image processing techniques: denoising, resampling, diffusion-weighted magnetic resonance imaging and apparent diffusion coefficient mapping.

3. The method according to claim 1, wherein detecting and segmenting in each of said radiographic images at least one regions of interest as reference ROI comprises, if the radiographic images are clinical images, detecting and segmenting in each clinical images at least one non-pathological regions of interest as reference ROI.

4. The method according to claim 3, wherein detecting and segmenting in each clinical image at least one non-pathological regions of interest as reference ROI, comprises segmenting various non-pathological anatomical structure of interest (ASIs), and segmenting and detecting ROIs in the segmented non-pathological ASIs.

5. The method according to claim 1, wherein detecting and segmenting in each of said radiographic images at least one regions of interest as reference ROI comprises, if the radiographic images are phantom images and/or mixed images each combining a patient and a pocket phantom, segmenting various phantom-derived structure of interest (PDSI) based on a reference material, and segmenting and detecting ROIs in the segmented PDSIs.

6. The method according to claim 1, further comprises, after detecting and segmenting at least one non-pathological regions of interest as reference ROI, optimizing at least one of the previously detected and segmented ROIs by at least one image processing technique chosen among binning of image values and rescaling.

7. The method according to claim 1, wherein measuring at least one radiomic feature per reference ROI comprises radiomics computing of each reference ROI.

8. The method according to claim 1, wherein identifying valid reference ROIs from a plurality of reference ROIs further comprises comparing the measured radiomics values to a predetermined range of radiomics values chosen from a set of reference value ranges and determining a valid reference ROI if the measured radiomics values thereof fall into the predetermined range of radiomics values.

9. The method according to claim 1, wherein clustering measured radiomics values of said valid reference ROIs into at least two reference clusters comprises classifying the measurements of valid reference ROIs into at least two clusters, and wherein clustering measured radiomics values of said valid reference ROIs into at least two reference clusters further comprises characterizing the at least two clusters in order to obtain at least two reference clusters.

10. A method for classifying at least one radiographic images according to a set of characteristics of image acquisition by applying a machine learning model generated for automatic classification of radiographic images, said machine learning model defining at least two reference clusters of said radiographic images acquired by various acquisition protocols, comprising:

Receiving at least one radiographic image,

Providing one of the at least one radiographic image as a candidate image for classification, Detecting and segmenting in said candidate image at least one region of interest as candidate reference ROI, Measuring at least one radiomic feature per candidate reference ROI, Identifying valid candidate reference ROIs from a plurality of candidate reference ROIs based on the measured radiomics values, Comparing the measured radiomics values of each said valid candidate reference ROIs to each of the radiomics value of each of said at least two reference clusters, and Classifying the candidate image into one of the at least two reference clusters based on the comparison.

11. The method according to claim 10, wherein the plurality of radiographic images comprises at least one kind of the following: clinical images being acquired by imaging a patient, phantom images acquired by imaging a phantom object, and mixed images each comprising a patient and a pocket phantom acquired by imaging a patient with a phantom object in proximity to the patient.

12. The method according to claim 11, comprises, before detecting and segmenting and after providing one of the at least one radiographic image as a candidate image for classification, selecting the machine learning model to be applied based on said candidate image for classification, comprising:

determining that the machine learning model to be applied is a first machine learning model being generated with clinical images if the candidate image is a clinical image;

determining that the machine learning model to be applied is a second machine learning model being generated with phantom images and/or mixed images if the candidate image is an image of a phantom object or a mixed image of a patient with a pocket phantom.

13. The method according to claim 10, wherein said machine learning model has been generated by implementing a method for generating a machine learning model according to claim 1.

14. The method according to claim 10, further comprising, before detecting and segmenting at least one ROIs as candidate reference ROI, pre-processing said candidate image by using at least one of the following image processing techniques: denoising, resampling, diffusion-weighted magnetic resonance imaging and apparent diffusion coefficient mapping.

15. The method according to claim 10, wherein detecting and segmenting in the candidate image at least one regions of interest as candidate reference ROI comprises, if it is determined that the machine learning model to be applied is the first machine learning model, detecting and segmenting in the candidate image at least one non-pathological regions of interest as candidate reference ROI.

16. The method according to claim 15, wherein detecting and segmenting in the candidate image at least one non-pathological regions of interest as candidate reference ROI comprises segmenting various non-pathological anatomical structure of interest, and segmenting and detecting ROIs in the segmented ASIs as candidate reference ROIs.

17. The method according to claim 10, wherein detecting and segmenting in the candidate image at least one region of interest as candidate reference ROI comprises, if it is determined that the machine learning model to be applied is the second machine learning model, segmenting various phantom-derived structure of interest, and segmenting and detecting ROIs in the segmented PDSIs.

18. The method according to claim 10, further comprises, after detecting and segmenting in the candidate image at least one region of interest as candidate reference ROI, optimizing at least one of the previously detected and segmented candidate reference ROIs by at least one image processing technique chosen among binning of image values and rescaling.

19. The method according to claim 10, wherein identifying valid candidate reference ROIs from a plurality of candidate reference ROIs further comprises comparing the measured radiomics values to a predetermined range of radiomics values chosen from a set of reference value ranges and determining a valid candidate reference ROI if the measured radiomics values thereof fall into the predetermined range of radiomics values.

20. The method according to claim 10, wherein comparing the measured radiomics values of each said valid candidate reference ROIs to each of the radiomics value of each of said at least two reference clusters comprises calculating distances between the measured radiomics values of each of the valid candidate reference ROIs and each of the radiomics values of each of the at least two reference clusters.

21. The method according to claim 10, wherein classifying the candidate image into one of the at least two reference clusters based on the comparison comprises selecting the cluster having the smallest calculated distance and/or eliminating the cluster having the largest calculated distance.

22. A computer program product comprising instructions which, when implemented by at least one digital processing device, performs at least ones among the method according to claim 1 and the method according to claim 10.

23. A method for generating a machine learning model for automatic classification of radiographic images acquired by various acquisition protocols, comprising:

Providing a plurality of radiographic images of at least two different patients, the radiographic images of each of the at least two different patients being acquired with acquisition protocols different from each other, Detecting and segmenting in each of said radiographic images at least one regions of interest as reference ROI, Measuring at least one radiomic feature per reference ROI, Identifying valid reference ROIs from a plurality of reference ROIs based on the measured radiomics values, Clustering the measured radiomics values of said valid reference ROIs into at least two reference clusters according to a set of characteristics of image acquisition, wherein detecting and segmenting in each of said radiographic images at least one regions of interest as reference ROI comprises, if the radiographic images are phantom images and/or mixed images each combining a patient and a pocket phantom, segmenting various phantom-derived structure of interest based on a reference material, and segmenting and detecting ROIs in the segmented PDSIs.

24. A method for generating a machine learning model for automatic classification of radiographic images acquired by various acquisition protocols, comprising:

Providing a plurality of radiographic images of at least two different patients, the radiographic images of each of the at least two different patients being acquired with acquisition protocols different from each other, Detecting and segmenting in each of said radiographic images at least one regions of interest as reference ROI, Measuring at least one radiomic feature per reference ROI, Identifying valid reference ROIs from a plurality of reference ROIs based on the measured radiomics values, Clustering the measured radiomics values of said valid reference ROIs into at least two reference clusters according to a set of characteristics of image acquisition, wherein identifying valid reference ROIs from a plurality of reference ROIs further comprises comparing the measured radiomics values to a predetermined range of radiomics values chosen from a set of reference value ranges and determining a valid reference ROI if the measured radiomics values thereof fall into the predetermined range of radiomics values.

* * * * *